US010098803B2

(12) United States Patent
Ito et al.

(10) Patent No.: US 10,098,803 B2
(45) Date of Patent: Oct. 16, 2018

(54) WALKING ASSIST DEVICE

(71) Applicant: HONDA MOTOR CO., LTD., Minato-Ku, Tokyo (JP)

(72) Inventors: Hisahiro Ito, Saitama (JP); Kazushi Hamaya, Saitama (JP); Tatsuya Noda, Saitama (JP)

(73) Assignee: Honda Motor Co., Ltd., Tokyo (JP)

( * ) Notice: Subject to any disclaimer, the term of this patent is extended or adjusted under 35 U.S.C. 154(b) by 452 days.

(21) Appl. No.: 14/828,894

(22) Filed: Aug. 18, 2015

(65) Prior Publication Data

US 2016/0051435 A1 Feb. 25, 2016

(30) Foreign Application Priority Data

Aug. 20, 2014 (JP) .................. 2014-167772

(51) Int. Cl.
*A61H 3/00* (2006.01)
*A61H 1/02* (2006.01)
*A61F 2/70* (2006.01)

(52) U.S. Cl.
CPC .................. *A61H 3/00* (2013.01); *A61F 2/70* (2013.01); *A61H 1/0244* (2013.01); *A61H 2003/007* (2013.01); *A61H 2201/1207* (2013.01); *A61H 2201/1238* (2013.01); *A61H 2201/164* (2013.01); *A61H 2201/165* (2013.01); *A61H 2201/1628* (2013.01)

(58) Field of Classification Search
CPC .. A61H 3/00; A61H 1/0244; A61H 2201/164; A61H 2201/1628; A61H 2201/1207; A61H 2201/1238; A61H 2201/165; A61H 2003/007; A61F 2/70
See application file for complete search history.

(56) References Cited

FOREIGN PATENT DOCUMENTS

JP 2010-000204 A 1/2010
JP 5081740 B2 11/2012

OTHER PUBLICATIONS

Office Action dated Aug. 1, 2017 issued in the counterpart Japanese patent application 2014-167772.

*Primary Examiner* — Sundhara Ganesan
(74) *Attorney, Agent, or Firm* — Carrier Blackman & Associates, P.C.; Joseph P. Carrier; Jingli Wang

(57) ABSTRACT

A main body frame 40 of a walking assist device 1, which is to be fixed to the waist of a user, has first frames 41 to be fixed to the waist of the user, second frames 42, and connection mechanisms 43, which connect the first frames 41 and the second frames 42 such that the relative positions of the second frames 42 with respect to the first frames 41 change according to the motions of the legs of the user.

4 Claims, 3 Drawing Sheets

WALKING ASSIST DEVICE

BACKGROUND OF THE INVENTION

Field of the Invention

The present invention relates to a walking assist device adapted to assist a user with walking.

Description of the Related Art

There has conventionally been known a walking assist device adapted to assist walking by applying a force output from a drive source (hereinafter referred to as "the assist force") to the legs of a person who has developed difficulty walking due to weakened muscle or the like (hereinafter referred to as "the user") (refer to, for example, Japanese Patent No. 5081740 (hereinafter referred to as "Patent Document 1")).

The walking assist device includes a drive source (electric motor), which outputs an assist force to assist the user with walking, a first orthosis (an abdominal belt and a lower back pad) to be attached to the waist of the user, second orthoses (thigh orthoses) to be attached to the legs of the user, a main body frame (back frame) to be fixed to the waist of the user by the first orthosis, and transmission members (power transmission arms), which connect the main body frame and the second orthoses and transmits an assist force to the legs of the user.

However, according to the configuration in which the main body frame, which is fixed to the waist of the user through the intermediary of the first orthosis, and the second orthoses fixed to the legs of the user are connected by the transmission members, as in the walking assist device described in Patent Document 1, there has been a danger of a stress being concentrated on a part of the main body frame or the transmission members, depending on the body shape of the user.

SUMMARY OF THE INVENTION

The present invention has been made in view of the background described above, and it is an object of the invention to provide a walking assist device adapted to minimize the chance of a stress being concentrated on a constituent member.

A walking assist device in accordance with the present invention includes: a drive source; a first orthosis adapted to be attached to the waist of a user; a second orthosis adapted to be attached to a leg of the user; a main body frame adapted to be fixed to the waist of the user by the first orthosis; and a transmission member that connects the main body frame and the second orthosis, wherein the transmission member transmits a force output from the drive source to a leg of the user, and the main body frame has a first frame adapted to be fixed to the waist of the user, a second frame to which the transmission member is connected, and a connection mechanism that connects the first frame and the second frame such that a relative position of the second frame with respect to the first frame changes according to a motion of a leg of the user.

In the walking assist device in accordance with the present invention, if a force that may generate a stress in the first frame constituting the main body frame, the second frame constituting the main body frame, or the transmission member, which constitutes the main body frame and which is connected to the second frame, is applied when the user is walking, then the connection mechanism changes the relative position of the second frame with respect to the first frame according to the motion of a leg of the user. This makes it possible to prevent the stress generated by the force applied to the main body frame from being concentrated on a constituent member of the main body frame or any part of the transmission members connected thereto.

Further, the walking assist device in accordance with the present invention is preferably provided with a restricting member that restricts a range in which the relative position of the second frame with respect to the first frame may change.

By having the restricting member, it is possible to easily restrict the range in which the relative position of the second frame with respect to the first frame may be changed to an appropriate range for obviating stress concentration or for ensuring the efficient transmission of an assist force.

Further, in the walking assist device in accordance with the present invention, the second frame is preferably movable in a direction along a lengthwise direction of the first frame.

Configuring the second frame to be movable in such a direction allows the second frame to smoothly move in response to a walking motion of the user, so that it is even easier to obviate stress concentration.

Further, in the walking assist device in accordance with the present invention, the connection mechanism preferably moves the second frame elastically with respect to the first frame.

The arrangement to elastically move the second frame prevents the moving direction of the second frame from being abruptly changed, so that the position at which a stress is concentrated will not be abruptly changed, thus making it possible to obviate the concentration of a stress that may be caused when the moving direction of the second frame is changed.

DESCRIPTION OF THE PREFERRED EMBODIMENTS

The following will describe a walking assist device according to an embodiment of the present invention with reference to the accompanying drawings.

Figure 1:
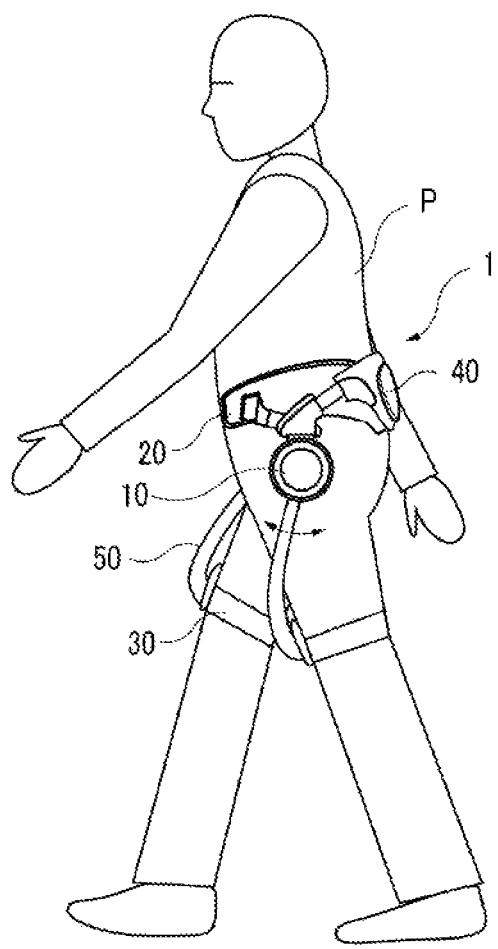
FIG. 1 is a side view illustrating a state in which a user is wearing a walking assist device according to an embodiment of the present invention.

Referring first to FIG. 1, a description will be given of the schematic configuration of a walking assist device 1 according to the present embodiment and an assist force applied to a user P.

As illustrated in FIG. 1, the walking assist device 1 includes electrically-operated actuators 10 (drive sources) that output an assist force for assisting the user P with walking, a waist orthosis 20 (first orthosis) to be attached to the waist of the user P, thigh orthoses 30 (second orthoses), which are to be attached, one each, to the thighs of the user P, a main body frame 40 to be fixed to the waist of the user P by the waist orthosis 20, and a pair of left and right power transmission arms 50 (transmission members), which connects the main body frame 40 and the thigh orthoses 30 and which transmits the assist force to the legs of the user P.

The actuators 10 are provided, one each, on both end parts of the main body frame 40 (refer to FIG. 2), and are positioned on the sides of the upper portions of the thighs or on the sides of the waist of the user P when attached. The power transmission arms 50 are provided, extending from both ends of the main body frame 40 toward the thighs of the user P. The thigh orthoses 30 are connected, one each, to the end portions of the power transmission arms 50 on the opposite side from the main body frame 40.

The force output from the actuators 10 causes the thigh orthoses 30 to swing in the longitudinal (front-back) direction of the user P through the intermediary of the power transmission arms 50. As a result, the force output from the actuators 10 acts on the user P as the assist force for assisting the walking.

Figure 2:
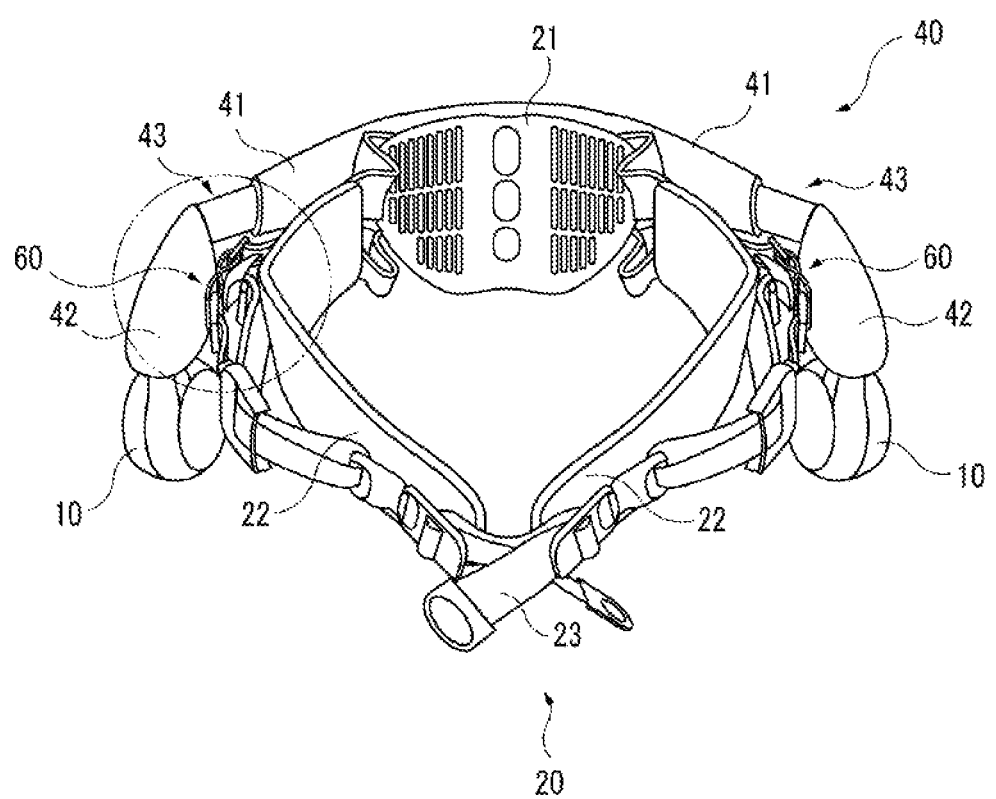
FIG. 2 is a front view of the walking assist device illustrated in FIG. 1.
Figure 3:
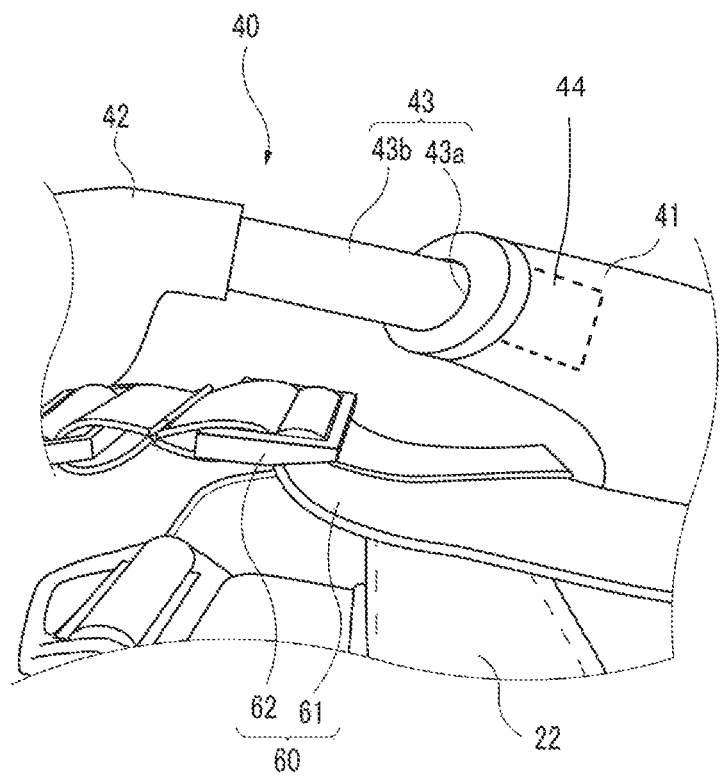
FIG. 3 is a plan view illustrating the configuration of the surroundings of a connection mechanism (the portion surrounded by a two-dot chain line in FIG. 2) of the walking assist device illustrated in FIG. 1.

Referring now to FIG. 2 and FIG. 3, a detailed description will be given of the structure of a section of the walking assist device 1 according to the present embodiment, the section being positioned around the waist of the user P.

As illustrated in FIG. 2, the waist orthosis 20 has a pad 21 positioned on the back side of the waist of the user P when attached, a pair of left and right belts 22 extending from the pad 21 to the front of the waist of the user P, and a fastener 23 provided at the end of the belt 22 on the opposite side from the pad 21. The pair of the belts 22 is releasably fastened with each other by the fastener 23. Further, the fastener 23 is provided with a length adjusting mechanism, which allows the fastening tightness of the waist orthosis 20 to be adjusted according to the body shape of the user P.

The main body frame 40 has first frames 41 fixed to the waist of the user P, a pair of left and right second frames 42 to which the power transmission arms 50 are connected, and connection mechanisms 43 which connect the first frames 41 and the second frames 42.

The first frames 41 are formed of arcuate members, which have both end portions thereof curved toward the second frames 42. The first frames 41 are fixed to the pad 21 of the waist orthosis 20 on the inner side of a central portion. Therefore, the first frames 41 are fixed at the back of the waist of the user P when attached.

The second frames 42 are provided, one each, on both end portions of the first frames 41, and are positioned on the sides of the upper portions of the thighs or the sides of the waist of the user P when attached. Further, each of the second frames 42 is provided with the actuator 10. The power transmission arms 50 are connected to the second frames 42 through the intermediary of the actuators 10 (refer to FIG. 1).

As illustrated in FIG. 3, each of the connection mechanisms 43 is composed of a bore 43a provided at the end portion of each of the first frames 41, a rod 43b, which is provided at the end portion of each of the second frames 42 that is adjacent to the first frame 41 and which is detachably and slidably inserted in the bore 43a, and a damper mechanism 44 provided in the first frame 41.

Each of the second frames 42 connected to the first frame 41 through the intermediary of the connection mechanism 43 is movable along the lengthwise direction of the first frame 41. As a result, the second frame 42 has a movement amount in the direction along the sagittal plane of the user P and a movement amount in the direction along the coronal plane of the user P. Further, the connection mechanisms 43 expand and contract elastically due to the damper mechanisms using springs or air springs.

Since the walking assist device 1 is provided with the connection mechanisms 43 as described above, if a force that may cause a stress to be generated in the first frames 41, the second frames 42 or the power transmission arms 50 connected to the second frames 42 while the user P is walking, then the relative positions of the second frames 42 with respect to the first frames 41 change according to a change in the motion of a leg of the user P. This makes it possible to prevent the stress generated from a force applied to the main body frame 40 from being concentrated on the constituent members of the main body frame 40 or a part of the power transmission arms 50 connected thereto.

Further, the connection mechanisms 43 elastically operate, so that the moving direction of the second frames 42 does not abruptly change and the position at which a stress is concentrated does not therefore abruptly change. As a result, excessive concentration of a stress can be obviated when the moving directions of the second frames 42 are changed.

The walking assist device 1 is provided with restricting belts 60 (restricting members) between the waist orthosis 20 and the main body frame 40.

Each of the restricting belts 60 is comprised of a belt 61, which extends from between the pad 21 of the waist orthosis 20 and the first frame 41 of the main body frame 40 toward the second frame 42 of the main body frame 40, and a buckle 62 attached to the second frame 42, and the length thereof is adjustable.

The range in which the relative positions of the second frames 42 with respect to the first frames 41 can be changed is adjusted by the restricting belts 60 according to the body shape of the user P. Thus, the range that permits the change can be set to an appropriate range for obviating the concentration of a stress or for efficiently transmitting an assist force.

The above has described the illustrated embodiment; however, the present invention is not limited thereto.

For example, in the foregoing embodiment, the main body frame 40 is fixed to the back of the waist of the user P through the intermediary of the pad 21 of the waist orthosis 20. Further, the thigh orthoses 30, which are the second orthoses, are fixed to the thighs of the user P. However, the fixing positions on the user of the walking assist device in accordance with the present invention are not limited to the foregoing positions. For example, the main body frame may be fixed to the front or a side of the waist of the user, or the second orthoses may be fixed to the crura.

Further, although the electrically-operated actuators 10 are used as the drive sources in the foregoing embodiment, the drive sources in the present invention are not limited to that type of configuration. For example, hydraulic actuators or the like may alternatively be used.

Further, in the foregoing embodiment, each of the connection mechanisms 43 is comprised of the bore 43a formed in the first frame 41 of the main body frame 40, the rod 43b, which is provided in the second frames 42 and which is detachably and slidably inserted in the bore 43a, and the damper mechanism provided in the first frame 41. However, the connection mechanisms in the present invention are not limited to such a constitution. For example, the connection mechanisms may alternatively be configured to connect the first frames and the second frames by using elastic members. Alternatively, the connection mechanisms may have no damper mechanism.

Further, in the foregoing embodiment, the connection mechanisms are configured to have the damper mechanisms such that the second frames elastically move regardless of whether the second frames move in the expanding direction or the contracting direction. However, the walking assist device in accordance with the present invention is not limited to such a configuration. For example, a configuration may be adopted such that the second frames elastically move only in either one direction in the expanding direction or the contracting direction.

Further, in the above embodiment, the thigh orthosis which is the second orthosis is fixed to each of the two legs of the user P. However, the walking assist device of the present invention may include only one second orthosis and it may be configured to be fixed to only one of the legs.

DESCRIPTION OF REFERENCE NUMERALS

1 . . . Walking assist device; 10 . . . Actuator (Drive source); 20 . . . Waist orthosis (First orthosis); 21 . . . Pad; 22 . . . Belt; 23 . . . Fastener; 30 . . . Thigh orthosis (Second orthosis); 40 . . . Main body frame; 41 . . . First frame; 42 . . . Second frame; 43 . . . Connection mechanism; 43a . . . Bore; 43b . . . Rod; 50 . . . Power transmission arm (Power transmission member); 60 . . . Restricting belt; 61 . . . Belt; and 62 . . . Buckle.

What is claimed is:

1. A walking assist device comprising:
a drive source;
a first orthosis adapted to be attached to a waist of a user;
a second orthosis adapted to be attached to a leg of the user;
a main body frame adapted to be fixed to the waist of the user by the first orthosis; and
a transmission member that connects the main body frame and the second orthosis, wherein
the transmission member transmits a force output from the drive source to the leg of the user,
the main body frame has a first frame adapted to be fixed to the waist of the user, a second frame to which the transmission member is connected, and a connection mechanism that connects the first frame and the second frame such that a relative position of the second frame with respect to the first frame changes according to a motion of the leg of the user, and
the connection mechanism is configured to move the second frame elastically with respect to the first frame.

2. The walking assist device according to claim 1, further comprising:
a restricting member that restricts a range in which the relative position of the second frame with respect to the first frame may change.

3. The walking assist device according to claim 1, wherein the second frame is movable in a direction along a lengthwise direction of the first frame.

4. The walking assist device according to claim 1, wherein the connection mechanism comprises:
a bore provided at end portion of the first frame,
a rod provided at end portion of the second frame and detachably and slidably inserted in the bore; and
a damper mechanism provided in the first frame.

* * * * *